(12) United States Patent
Champion

(10) Patent No.: US 10,239,820 B2
(45) Date of Patent: Mar. 26, 2019

(54) ETHERAMINE COMPOUNDS

(71) Applicant: Huntsman Petrochemical LLC, The Woodlands, TX (US)

(72) Inventor: Donald H Champion, Spring, TX (US)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 0 days.

(21) Appl. No.: 15/523,418

(22) PCT Filed: Dec. 1, 2015

(86) PCT No.: PCT/US2015/063062
§ 371 (c)(1),
(2) Date: May 1, 2017

(87) PCT Pub. No.: WO2016/089798
PCT Pub. Date: Jun. 9, 2016

(65) Prior Publication Data
US 2017/0313647 A1    Nov. 2, 2017

Related U.S. Application Data

(60) Provisional application No. 62/087,718, filed on Dec. 4, 2014.

(51) Int. Cl.
| | | |
|---|---|---|
| *C07C 217/08* | (2006.01) | |
| *C07C 255/13* | (2006.01) | |
| *C07C 213/02* | (2006.01) | |
| *C07C 253/30* | (2006.01) | |

(52) U.S. Cl.
CPC .......... *C07C 217/08* (2013.01); *C07C 213/02* (2013.01); *C07C 253/30* (2013.01); *C07C 255/13* (2013.01); *C07C 2601/14* (2017.05)

(58) Field of Classification Search
CPC ... C07C 217/08; C07C 255/13; C07C 213/02; C07C 253/30; C07C 2601/14; C07C 2101/14
See application file for complete search history.

(56) References Cited

U.S. PATENT DOCUMENTS

| | | | |
|---|---|---|---|
| 3,324,164 A * | 6/1967 | Corr ........................ | C07B 61/00 558/389 |
| 5,932,526 A | 8/1999 | Person Hei et al. | |
| 6,576,794 B2 | 6/2003 | Fukushima et al. | |
| 2009/0143623 A1 * | 6/2009 | Katsumata ............ | C07C 255/13 568/589 |

* cited by examiner

*Primary Examiner* — Valerie Rodriguez-Garcia
(74) *Attorney, Agent, or Firm* — Huntsman Petrochemical LLC; Edward Korompai

(57) ABSTRACT

Embodiments described herein provide a compound that may be used in a variety of applications such as corrosion inhibition, additives for metalworking, mining reagents, epoxy curatives, emulsifiers, fuel or lubricant additives, surfactant manufacture, acid scavengers and asphalt additives. The compound has the following structure:

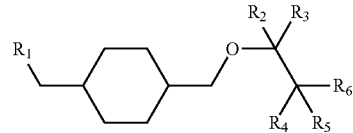

where $R_1$ is a methoxy group,
$R_2$, $R_3$, $R_4$ and $R_5$ are independently a hydrogen atom or an alkyl group, and
$R_6$ is an aminomethyl group.

18 Claims, No Drawings

ETHERAMINE COMPOUNDS

CROSS-REFERENCE TO RELATED APPLICATIONS

This application is the National Phase of International Application PCT/US2015/063062 filed Dec. 1, 2015 which designated the U.S. and which claims priority to U.S. App. Ser. No. 62/087,718 filed Dec. 4, 2014. The noted applications are incorporated herein by reference.

FIELD

Embodiments described herein are generally related to aliphatic etheramines, and more specifically, to a cycloaliphatic etheramine.

BACKGROUND

Etheramines prepared from acrylonitrile are known as alkyloxypropylamines, which are used in a variety of applications such as corrosion inhibition, additives for metalworking, mining reagents, epoxy curatives, emulsifiers, fuel or lubricant additives, surfactant manufacture, acid scavengers and asphalt additives.

SUMMARY

Embodiments described herein provide an etheramine compound that may be used in a variety of applications such as corrosion inhibition, additives for metalworking, mining reagents, epoxy curatives, emulsifiers, fuel or lubricant additives, surfactant manufacture, acid scavengers and asphalt additives. The compound has the following structure:

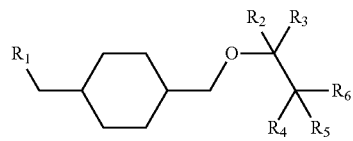

where $R_1$ is a hydrogen atom or a methoxy group,
$R_2$, $R_3$, $R_4$ and $R_5$ are independently a hydrogen atom or an alkyl group, and
$R_6$ is an aminomethyl group.

In another embodiment, an etheramine compound includes the following structure:

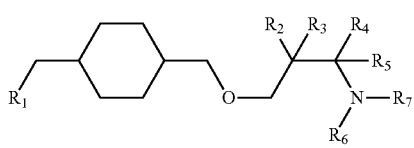

where $R_6$ has the structure

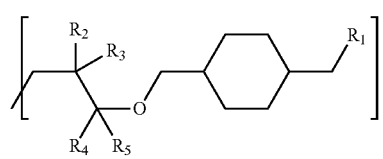

$R_7$ is a hydrogen atom or the same as $R_6$,
$R_1$ is a hydrogen atom or a methoxy group, and
$R_2$, $R_3$, $R_4$ and $R_5$ are independently a hydrogen atom or an alkyl group.

In another embodiment, a method for forming an etheramine compound includes reacting 4-methylcyclohexane methanol or 4-methoxymethylcyclohexane methanol with an alkene having a nitrile group to form an intermediate compound having the structure:

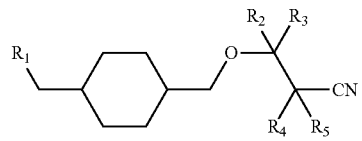

where $R_1$ is a hydrogen atom or a methoxy group and $R_2$, $R_3$, $R_4$ and $R_5$ are independently a hydrogen atom or an alkyl group, and hydrogenating the intermediate compound to form the etheramine compound having the structure:

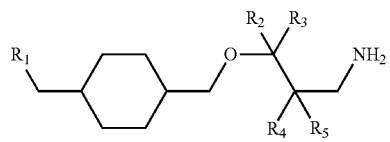

where $R_1$ is a hydrogen atom or a methoxy group and $R_2$, $R_3$, $R_4$ and $R_5$ are independently a hydrogen atom or an alkyl group.

In another embodiment, an etheramine compound is formed by a method including reacting 4-methylcyclohexane methanol or 4-methoxymethylcyclohexane methanol with an alkene having a nitrile group to form an intermediate compound having the structure:

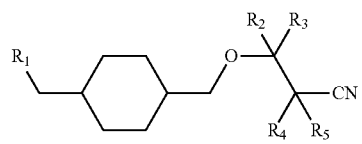

where $R_1$ is a hydrogen atom or a methoxy group and $R_2$, $R_3$, $R_4$ and $R_5$ are independently a hydrogen atom or an alkyl group, and hydrogenating the intermediate compound.

DETAILED DESCRIPTION

Embodiments described herein provide an etheramine compound that may be used in a variety of applications such as corrosion inhibition, additives for metalworking, mining reagents, epoxy curatives, emulsifiers, fuel or lubricant additives, surfactant manufacture, acid scavengers and asphalt additives. The etheramine compound has the following structure:

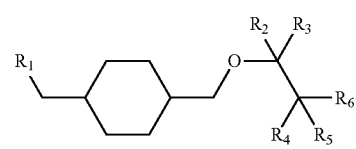

where $R_1$ is a hydrogen atom or a methoxy group,
$R_2$, $R_3$, $R_4$ and $R_5$ are independently a hydrogen atom or an alkyl group, and
$R_6$ is an aminomethyl group.

The etheramine compound may also have the structure:

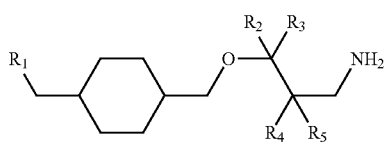

(I)

where $R_1$ is a hydrogen atom or a methoxy group and $R_2$, $R_3$, $R_4$ and $R_5$ are independently a hydrogen atom or an alkyl group.

An etheramine compound having the structure:

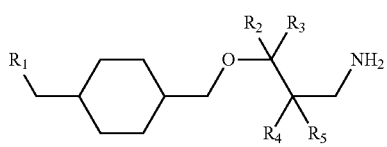

(I)

where $R_1$ is a hydrogen atom or a methoxy group and $R_2$, $R_3$, $R_4$ and $R_5$ are independently a hydrogen atom or an alkyl group, may be used in a variety of applications such as corrosion inhibition, additives for metalworking, mining reagents, epoxy curatives, emulsifiers, fuel or lubricant additives, surfactant manufacture, acid scavengers and asphalt additives.

The etheramine compound may be formed by reacting 4-methylcyclohexane methanol or 4-methoxymethylcyclohexane methanol with an alkene having a nitrile group to form an intermediate compound having the following structure:

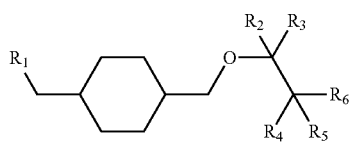

where $R_1$ is a hydrogen atom or a methoxy group,
$R_2$, $R_3$, $R_4$ and $R_5$ are independently a hydrogen atom or an alkyl group, and
$R_6$ is a nitrile group.

The intermediate compound may also have the structure:

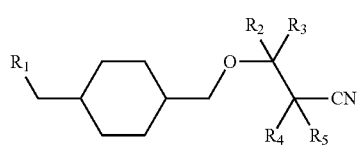

(II)

where $R_1$ is a hydrogen atom or a methoxy group and $R_2$, $R_3$, $R_4$ and $R_5$ are independently a hydrogen atom or an alkyl group.

The alkene having a nitrile group may be acrylonitrile or any suitable straight or branched alkene having a nitrile group. The reaction temperature may range from about −20 degrees Celsius to about 60 degrees Celsius, such as from about 19 degrees Celsius to about 33 degrees Celsius.

The reaction between 4-methylcyclohexane methanol or 4-methoxymethylcyclohexane methanol and the alkene having a nitrile group may be a cyanoethylation reaction. In one embodiment, acrylonitrile is reacted with 4-methylcyclohexane methanol or 4-methoxymethylcyclohexane methanol in a cyanoethylation reaction. The cyanoethylation reaction may be reversible and equilibrium limited. Using an excess of acrylonitrile can provide a higher alcohol conversion. A base catalyst may be used to facilitate the reaction of the alcohols. Suitable base catalysts include alkali hydroxides, and alkali alkoxides such as sodium methylate, amines, guanidines, or solid bases such as KF on alumina. At the end of the cyanoethylation reaction the catalyst may be neutralized to limit byproduct formation. Any solvent that does not interfere with the reaction may also be employed.

Hydrogenation of the intermediate compound may be performed by reacting the intermediate compound with hydrogen gas to form the etheramine compound. The etheramine compound having the structure (I) may be a primary amine. Alternatively, the etheramine compound may be a secondary amine or tertiary amine having the following structure:

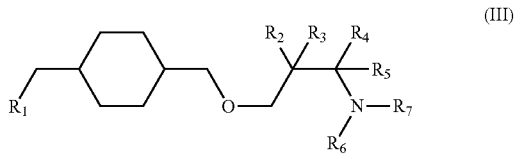

(III)

where $R_6$ has the following structure:

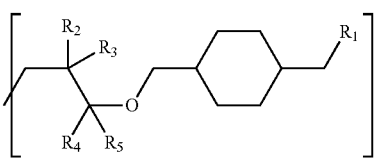

(IV)

$R_7$ is a hydrogen atom or the same as $R_6$,
$R_1$ is a hydrogen atom or a methoxy group, and
$R_2$, $R_3$, $R_4$ and $R_5$ are independently a hydrogen atom or an alkyl group.

Different catalyst used in the hydrogenation reaction between the intermediate compound and hydrogen gas may determine whether the etheramine compound is a primary amine, secondary amine or tertiary amine. Primary means that the etheramine compound includes at least 40% by weight of the primary amine. For example, a cobalt catalyst may cause the etheramine compound to be a primary amine, such that the amount of primary amine in the etheramine compound may be over 80% by weight. Secondary means that the etheramine compound includes at least 40% by weight of the secondary amine. For example, a nickel catalyst may cause the etheramine compound to be a secondary amine, such that the amount of secondary amine in the etheramine compound is over 40% by weight. Tertiary means that the etheramine compound includes at least 40% by weight of the tertiary amine. For example, a platinum catalyst may cause the etheramine compound to be a tertiary amine, such that the amount of tertiary amine in the etheramine compound is over 40% by weight. Formation of a primary amine may be also increased by the presence of ammonia in the hydrogenation reaction mixture to limit coupling at the nitrogen of the amine and the nitrile carbon.

The hydrogenation reaction may be carried out catalytically in batch or continuous reactors. Reduction with a hydrogen donor can also be applied stoichiometrically. The hydrogenation reaction may be performed at a temperature between about 20 degrees Celsius and about 140 degrees Celsius, such as between about 80 degrees Celsius and about 120 degrees Celsius. The hydrogenation reaction may be performed between about 14.3 psig and about 2000 psig.

In one embodiment, the etheramine compound is 3-[(4-methylcyclohexyl)methyloxy]-1-propanamine and has the following structure:

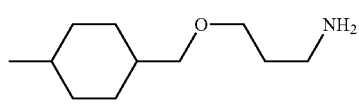
(V)

The 3-[(4-methylcyclohexyl)methyloxy]-1-propanamine may be formed by reacting 4-methylcyclohexane methanol with acrylonitrile to form 3-[(4-methylcyclohexyl)methyloxy]-1-propanenitrile, which has the following structure:

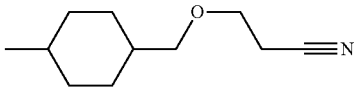
(VI)

3-[(4-methylcyclohexyl)methyloxy]-1-propanenitrile is then hydrogenated in the presence of a cobalt catalyst and ammonia to form 3-[(4-methylcyclohexyl)methyloxy]-1-propanamine, although secondary and tertiary amines may be present. If the catalyst used in the hydrogenation reaction is a nickel catalyst and no ammonia is present in the reaction mixture, the product of the hydrogenation reaction may be iminobis{3-[(4-methylcyclohexyl)methyloxy]propane, which is a secondary amine having the following structure:

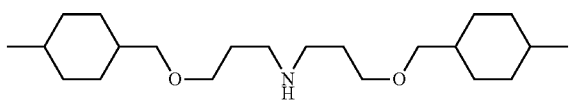
(VII)

If the catalyst used in the hydrogenation reaction is a platinum catalyst and no ammonia is present in the reaction mixture, the product of the hydrogenation reaction may be a tertiary amine having the following structure:

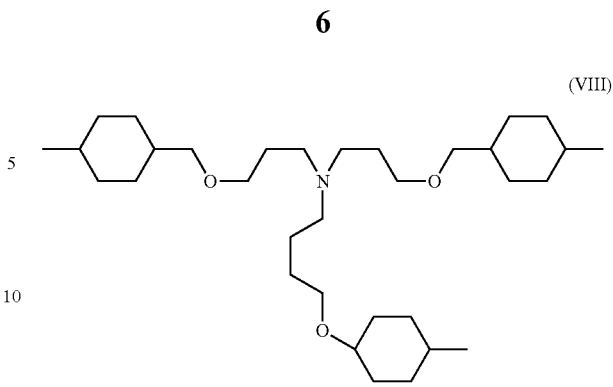
(VIII)

In one embodiment, a reactant, which is a mixture of 4-methylcyclohexane methanol and 4-methoxymethylcyclohexane methanol, is reacted with acrylonitrile to form an intermediate compound, which is a mixture of 3-[(4-methylcyclohexyl)methyloxy]-1-propanenitrile and 3-[(4-methoxy methylcyclohexyl)methyloxy]-1-propanenitrile, which has the following structure:

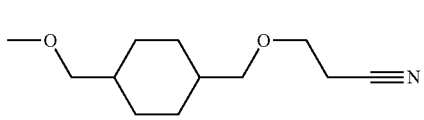
(IX)

The intermediate compound is then hydrogenated with a cobalt catalyst and ammonia to form an etheramine compound, which is a mixture of 3-[4(4-methylcyclohexyl)methyloxy]-1-propanamine and 3-[(4-methoxy methylcyclohexyl)methyloxy]-1-propanamine, which has the following structure:

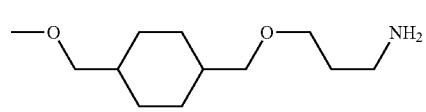
(X)

If the catalyst used in the hydrogenation reaction is a nickel catalyst and ammonia is not added to the reaction mixture, the etheramine compound formed by the hydrogenation reaction may be a mixture of iminobis{3-[(4-methylcyclohexyl)methyloxy]}propane and N-3-[(4-methyloxy methylcyclohexyl)methyloxy]propyl-3-[4-methylcyclohexyl]methyloxy]-1-propanamine, which has the following structure:

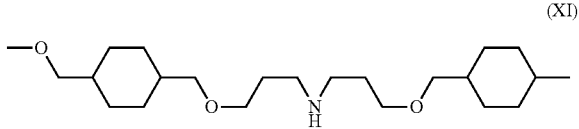
(XI)

The etheramine compound, such as 3-[(4-methylcyclohexyl)methyloxy]-1-propanamine, 3-[(4-methoxy methylcyclohexyl)methyloxy]-1-propanamine, iminobis{3-[(4-methylcyclohexyl)methyloxy]}propane or N-3-[(4-methyloxy methylcyclohexyl)methyloxy]propyl-3-[4-methylcyclohexyl]methyloxy]-1-propanamine, is a novel etheramine compound that may be used as corrosion inhibitors, additives for metal working, silica flotation aids for the beneficiation of iron or phosphate ores, epoxy curatives, emulsifiers, fuel or lubricant additives, acid scavengers and asphalt additives. The etheramine compound may be also used as a starting material to form ethoxylated amine, amine oxide, quaternary ammonium or amphoteric surfactants. The intermediate compounds, such as 3-[(4-methylcyclohexyl)methyloxy]-1-propanenitrile and 3-[(4-methoxy methylcyclohexyl)methyloxy]-1-propanenitrile, are also novel compounds.

The following examples are provided as illustrative examples and shall not be construed as delimitive of the scope of the disclosure whatsoever.

In one example, crude 4-methylcyclohexane methanol is used as the starting material. 4-methylcyclohexane methanol is a byproduct from the manufacture of cyclohexanedimethanol. The starting material, crude 4-methylcyclohexane methanol, in the following experiments, contained 4-5% water, 81% 4-methoxymethylcyclohexane methanol, 5% 4-methoxymethylcyclohexane methanol, and other impurities. Crude 4-methylcyclohexane methanol was reacted with excess acrylonitrile using sodium methylate catalyst to give an intermediate compound, which is a liquid containing suspended and crystallized solids. The intermediate compound was analyzed using gas chromatography-mass spectrometry, which identified peaks associated with 3-[(4-methylcyclohexyl)methyloxy]-1-propanenitrile and 3-[(4-methoxy methylcyclohexyl)methyloxy]-1-propanenitrile.

In another example, distillation of crude 4-methylcyclohexane methanol was conducted to remove water. The resulting 4-methylcyclohexane methanol has 0.7% water by weight and a hydroxyl number of 427 mg KOH/g. Cyanoethylation was carried out by addition of acrylonitrile by syringe pump to catalyzed 4-methylcyclohexane methanol (sodium methylate was used as the catalyst). 1997.98 g of 4-methylcyclohexane methanol (15.20 equivalents) was reacted with 835.7 g (15.75 mol) of acrylonitrile in the presence of 5.26 g sodium methylate at a temperature between about 19 degrees Celsius and about 33 degrees Celsius. The acrylonitrile was added over a period of about two hours. Infrared spectrophotometry analysis of the reaction mixture indicated about 69% conversion. Another 5.26 g of sodium methylate was added and the mixture was stirred for two hours and found to contain significant unreacted alcohol. After stirring for about six hours an additional 48.2 g of acrylonitrile was added. The mixture was allowed to further react at about 20 degrees Celsius for 24 hours. Then 3.63 g of acetic acid was added along with 23.5 g magnesium silicate and the slurry was heated to about 80 degrees Celsius. The slurry was vacuum stripped at about 80 degrees Celsius and then filtered to obtain 2748 g of a clear and nearly colorless liquid having a hydroxyl number of 8.87 mg KOH/g, 0.5 ppm K and 0.8 ppm Na. The clear and nearly colorless liquid was identified to be 3-[(4-methylcyclohexyl)methyloxy]-1-propanenitrile.

The 3-[(4-methylcyclohexyl)methyloxy]-1-propanenitrile was hydrogenated in a tubular reactor over a solid form cobalt catalyst in the presence of ammonia at about 120 degrees Celsius and 2000 psig. 3-[(4-methylcyclohexyl)methyloxy]-1-propanenitrile was fed into the reactor at a rate of 100 g/h, ammonia was fed into the reactor at a rate of 70 g/h, and hydrogen gas was fed into the reactor at a rate of 50 l/h. The effluent was a dark amber-orange liquid. The dark amber-orange liquid was vacuum stripped to remove lights and analyzed. Gas chromatography/mass spectrometry gave m/z 185 for the major peaks, along with m/z 215, 353 and 383 for minor peaks. These correspond to 3-[(4-methylcyclohexyl)methyloxy]-1-propanamine, 3-[(4-methoxy methylcyclohexyl)methyloxy]-1-propanamine, iminobis{3-[(4-methylcyclohexyl)methyloxy]}propane and N-3-[(4-methyloxy methylcyclohexyl)methyloxy]propyl-3-[4-methylcyclohexyl]methyloxy]-1-propanamine. Nuclear magnetic resonance confirmed the presence of 3-[(4-methylcyclohexyl)methyloxy]-1-propanamine and 3-[(4-methoxy methylcyclohexyl)methyloxy]-1-propanamine.

The etheramine compound, such as 3-[(4-methylcyclohexyl)methyloxy]-1-propanamine, 3-[(4-methoxy methylcyclohexyl)methyloxy]-1-propanamine, iminobis{3-[(4-methylcyclohexyl)methyloxy]}propane or N-3-[(4-methyloxy methylcyclohexyl)methyloxy]propyl-3-[4-methylcyclohexyl]methyloxy]-1-propanamine, may be used for silica flotation in iron beneficiation. As high iron ores have been depleted, minerals with a lower iron concentration are processed to meet iron demand. Smelters require iron concentrations higher than concentration found in presently mined ores, thus forcing the use of separation processes to beneficiate the iron. Silica is found along with iron in the mined ores. A commonly used separation process is the reverse flotation of silica. Silica gangue is removed by flotation in water, concentrating the iron by leaving the iron behind, hence the term reverse flotation. Before performing the reverse flotation, the slime formed by small particles may be beneficially removed by hydromechanical means. The etheramine compound may act as a collector to enhance the floatability of different mineral materials. The compound may act both as a collector and a frother, which is used to promote the creation of a semi-stable froth.

The etheramine compound, such as 3-[(4-methylcyclohexyl)methyloxy]-1-propanamine, 3-[(4-methoxy methylcyclohexyl)methyloxy]-1-propanamine, iminobis{3[(4-methylcyclohexyl)methyloxy]}propane or N-3-[(4-methyloxy methylcyclohexyl)methyloxy]propyl-3-[4-methylcyclohexyl]methyloxy]-1-propanamine, may be used for curing of an epoxy resin. In one example, the etheramine compound having hydrogen equivalent mass of 98.0 (4.90 g) was mixed with ARALDITE® GY1610, which is a liquid epoxy resin with equivalent mass of 183 (9.15 g), in an aluminum weighing pan. Upon standing overnight, the mixture became a hard, brittle solid.

While the foregoing is directed to embodiments of the present invention, other and further embodiments of the invention may be devised without departing from the basic scope thereof, and the scope thereof is determined by the claims that follow.

The invention claimed is:
1. A compound having the structure:

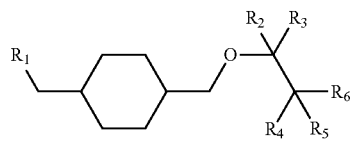

wherein $R_1$ is a hydrogen atom or a methoxy group,
$R_2$, $R_3$, $R_4$ and $R_5$ are independently a hydrogen atom or an alkyl group, and
$R_6$ is a nitrile group or an aminomethyl group.
2. The compound of claim 1, wherein the compound has the structure:

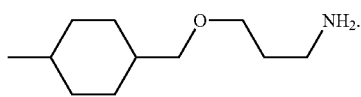

3. The compound of claim 1, wherein the compound has the structure:

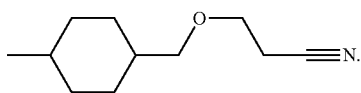

4. The compound of claim 1, wherein the compound has the structure:

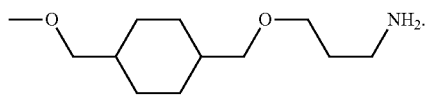

5. The compound of claim 1, wherein the compound has the structure:

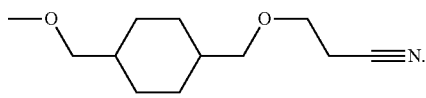

6. An etheramine compound having the structure:

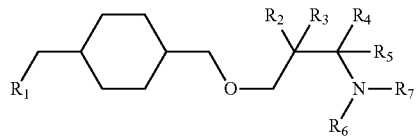

wherein $R_6$ has the structure

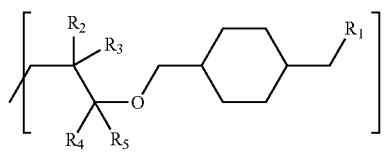

$R_7$ is a hydrogen atom or the same as $R_6$,
$R_1$ is a hydrogen atom or a methoxy group, and
$R_2$, $R_3$, $R_4$ and $R_5$ are independently a hydrogen atom or an alkyl group.

7. The etheramine compound of claim 6, wherein the etheramine compound has the structure:

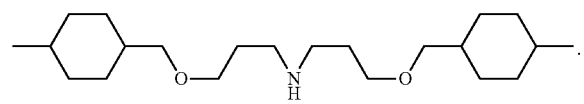

8. The etheramine compound of claim 6, wherein the etheramine compound has the structure:

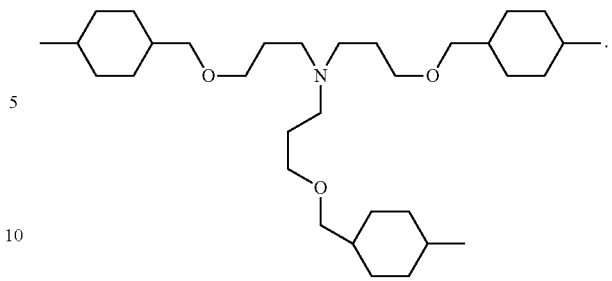

9. The etheramine compound of claim 6, wherein the etheramine compound has the structure:

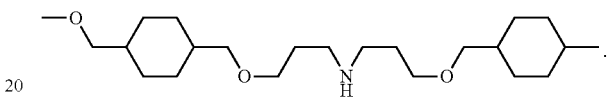

10. A method for forming an etheramine compound, comprising:
reacting 4-methylcyclohexane methanol or 4-methoxymethylcyclohexane methanol with an alkene having a nitrile group to form an intermediate compound having the structure:

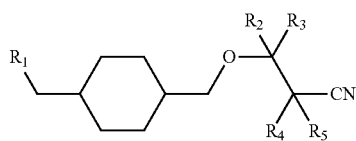

wherein $R_1$ is a hydrogen atom or a methoxy group and $R_2$, $R_3$, $R_4$ and $R_5$ are independently a hydrogen atom or an alkyl group; and
hydrogenating the intermediate compound to form the etheramine compound having the structure:

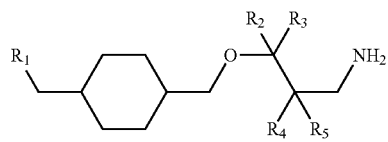

wherein $R_1$ is a hydrogen atom or a methoxy group and $R_2$, $R_3$, $R_4$ and $R_5$ are independently a hydrogen atom or an alkyl group.

11. The method of claim 10, wherein the alkene having the nitrile group is acrylonitrile.

12. The method of claim 10, wherein a cobalt catalyst is used for the hydrogenating of the intermediate compound.

13. The method of claim 12, wherein the etheramine compound has the structure:

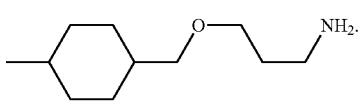

14. An etheramine compound formed by a method comprising:

reacting 4-methylcyclohexane methanol or 4-methoxymethylcyclohexane methanol with an alkene having a nitrile group to form an intermediate compound having the structure:

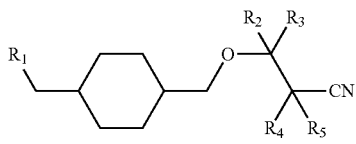

wherein $R_1$ is a hydrogen atom or a methoxy group and $R_2$, $R_3$, $R_4$ and $R_5$ are independently a hydrogen atom or an alkyl group; and hydrogenating the intermediate compound.

15. The etheramine compound of claim 14, wherein the etheramine compound has the structure:

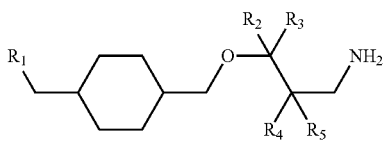

wherein $R_1$ is a hydrogen atom or a methoxy group and $R_2$, $R_3$, $R_4$ and $R_5$ are independently a hydrogen atom or an alkyl group.

16. The etheramine compound of claim 15, wherein the etheramine compound has the structure:

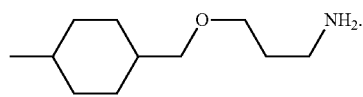

17. A method for forming an etheramine compound comprising:

reacting 4-methylcyclohexane methanol or 4-methoxymethylcyclohexane methanol with an alkene having a nitrile group to form an intermediate compound having the structure:

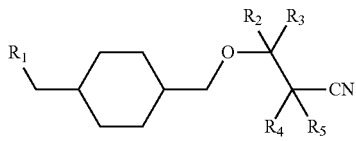

wherein $R_1$ is a hydrogen atom or a methoxy group and $R_2$, $R_3$, $R_4$ and $R_5$ are independently a hydrogen atom or an alkyl group; and hydrogenating the intermediate compound in the absence of ammonia using a nickel catalyst to form the etheramine compound having the structure:

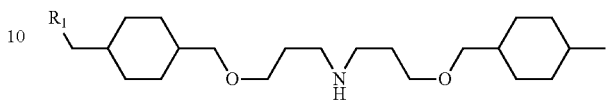

wherein $R_1$ is a hydrogen atom or a methoxy group.

18. A method for forming an etheramine compound comprising:

reacting 4-methylcyclohexane methanol with an alkene having a nitrile group to form an intermediate compound having the structure:

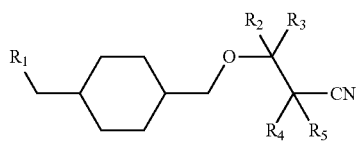

wherein $R_1$ is a hydrogen atom and $R_2$, $R_3$, $R_4$ and $R_5$ are independently a hydrogen atom or an alkyl group; and hydrogenating the intermediate compound using a platinum catalyst to form the etheramine compound having the structure:

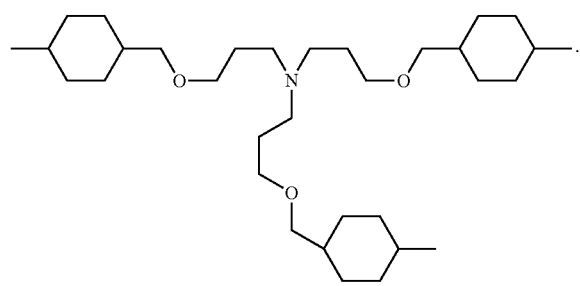

* * * * *